US007927856B2

(12) United States Patent
Ho et al.

(10) Patent No.: US 7,927,856 B2
(45) Date of Patent: Apr. 19, 2011

(54) THERMOPHILIC ENDO-GLUCANASE AND USES THEREOF

(75) Inventors: Tuan-Hua David Ho, Taipei (TW); Su-May Yu, Taipei (TW); I Son Ng, Tainan (TW); Chii-Gong Tong, Tainan County (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 12/541,322

(22) Filed: Aug. 14, 2009

(65) Prior Publication Data

US 2010/0047869 A1    Feb. 25, 2010

Related U.S. Application Data

(60) Provisional application No. 61/089,100, filed on Aug. 15, 2008.

(51) Int. Cl.
*C12N 9/24* (2006.01)
*C07H 21/04* (2006.01)
*C12N 15/00* (2006.01)
*C12N 1/20* (2006.01)

(52) U.S. Cl. ............... 435/200; 435/252.3; 435/252.33; 435/320.1; 536/23.2

(58) Field of Classification Search ............... None
See application file for complete search history.

(56) References Cited

U.S. PATENT DOCUMENTS

| | | |
|---|---|---|
| 5,677,151 A | 10/1997 | Wilson et al. |
| 6,451,063 B1 | 9/2002 | Clarkson et al. |
| 6,602,700 B1 | 8/2003 | Li et al. |
| 7,041,488 B2 | 5/2006 | Outtrup et al. |
| 7,141,403 B2 | 11/2006 | Outtrup et al. |
| 7,220,565 B2 | 5/2007 | Brown et al. |
| 7,226,773 B2 | 6/2007 | Schulein et al. |
| 7,273,748 B2 | 9/2007 | Miettinen-Oinonen et al. |
| 2007/0166805 A1 | 7/2007 | Cosgrove et al. |
| 2007/0238155 A1 | 10/2007 | Gusakov et al. |
| 2008/0131958 A1 | 6/2008 | Remmereit et al. |

*Primary Examiner* — Nashaat T Nashed
(74) *Attorney, Agent, or Firm* — Occhiuti Rohlicek & Tsao LLP (57) ABSTRACT

A novel thermophilic endo-glucanase, nucleic acid encoding the endo-glucase, and uses thereof in converting lignocellulosic material to fermentable sugars.

11 Claims, 6 Drawing Sheets

```
  1 ATG GAA CGC ACC CCG GTG GAA GAA AAC GGC CGC CTG CAG GTG GTG GGC ACC GCG CTG CTG
  1  M   E   R   T   P   V   E   E   N   G   R   L   Q   V   V   G   T   A   L   L

61 AAC CAG CAT AAC AAA CCG TTT CAG CTG CGC GGC ATT AGC ACC CAT GGC CTG CAG TGG TTT
 21  N   Q   H   N   K   P   F   Q   L   R   G   I   S   T   H   G   L   Q   W   F

121 GGC CAG TTT GCG AAC AAA GAT GCG TTT CAG ACC CTG CGC GAT GAT TGG AAA GCG AAC GTG
 41  G   Q   F   A   N   K   D   A   F   Q   T   L   R   D   D   W   K   A   N   V

181 GTG CGC CTG GCG ATG TAT ACC GAT CCG AAC GCG AAC GGC TAT ATT GCG CAG CCG GAA TGG
 61  V   R   L   A   M   Y   T   D   P   N   A   N   G   Y   I   A   Q   P   E   W

241 CTG AAA GCG AAA GTG AAA GAA GGC GTG CAG GCG GCG CTG GAT CTG GGC ATG TAT GTG ATT
 81  L   K   A   K   V   K   E   G   V   Q   A   A   L   D   L   G   M   Y   V   I

301 ATT GAT TGG CAT ATT CTG AAC GAT AAC GAT CCG AAC CTG TAT AAA GAA CAG GCG AAA CGC
101  I   D   W   H   I   L   N   D   N   D   P   N   L   Y   K   E   Q   A   K   R

361 TTT TTT GCG GAA ATG GCG CGC GAA TAT GGC AAA TAT CCG AAC GTG ATT TAT GAA ATT GCG
121  F   F   A   E   M   A   R   E   Y   G   K   Y   P   N   V   I   Y   E   I   A

421 AAC GAA CCG AAC GGC AAC GAT GTG ACC TGG GAA GAA AAA ATT CGC CCG TAT GCG GAT GAA
141  N   E   P   N   G   N   D   V   T   W   E   E   K   I   R   P   Y   A   D   E

461 GTG ATT CGC ACC ATT CGC AGC ATT GAT CGC GAT AAC CTG ATT ATT GTG GGC ACC GGC ACC
161  V   I   R   T   I   R   S   I   D   R   D   N   L   I   I   V   G   T   G   T

521 TGG AGC CAG GAT GTG GAT GAT GTG GCG AGC GAT CCG CTG CCG TAT AAA AAC ATT ATG TAT
181  W   S   Q   D   V   D   D   V   A   S   D   P   L   P   Y   K   N   I   M   Y

581 GCG GTG CAT TTT TAT AGC GGC ACC CAT ACC CAG TGG CTG CGC GAT CGC GTG GAT GCG GCG
201  A   V   H   F   Y   S   G   T   H   T   Q   W   L   R   D   R   V   D   A   A

641 CTG CAG GCG GGC ACC CCG GTG TTT GTG AGC GAA TGG GGC ACC AGC GAT GCG AGC GGC GAT
221  L   Q   A   G   T   P   V   F   V   S   E   W   G   T   S   D   A   S   G   D

701 GGC GGC CCG TAT CTG GAA GAA GCG GAA AAA TGG ATT GAA TTT CTG AAC GAA CGC GGC ATT
241  G   G   P   Y   L   E   E   A   E   K   W   I   E   F   L   N   E   R   G   I

761 AGC TGG GTG AAC TGG AGC CTG TGC GAT AAA AAC GAA GCG AGC GCG GCG CTG CGC CCG GGC
261  S   W   V   N   W   S   L   C   D   K   N   E   A   S   A   A   L   R   P   G

821 GCG GAT CCG CAT GGC GGC TGG GGC GAT GAT CAT CTG AGC GAT AGC GGC CGC TTT ATT AAA
281  A   D   P   H   G   G   W   G   D   D   H   L   S   D   S   G   R   F   I   K

881 GCG AAA CTG ATT GAA GCG GCG CAG CAG AGC GGC CAG AAA GCG AAA GGC GCG GCG AAC CCG
301  A   K   L   I   E   A   A   Q   Q   S   G   Q   K   A   K   G   A   A   N   P

941 CAT CAG CGC AAC GGC AAC GAT AGC AGC GAT GCC GGC AAA ACC GGC CAT GCG AGC GGC CAT
321  H   Q   R   N   G   N   D   S   S   D   G   G   K   T   G   H   A   S   G   H

1001 CCG TTT TTT TGG ACC TTT ATT CTG GCG GCG GGC GTG GCG TTT GGC TTT GGC GGC CTG GCG
341   P   F   F   W   T   F   I   L   A   A   G   V   A   F   G   F   G   G   L   A

1061 CTG GGC AAA CGC CTG TTT AAA GAA
361   L   G   K   R   L   F   K   E
```

THERMOPHILIC ENDO-GLUCANASE AND USES THEREOF

RELATED APPLICATION

This application claims priority to U.S. Provisional Application No. 61/089,100, filed on Aug. 15, 2008, the content of which is hereby incorporated by reference in its entirety.

BACKGROUND OF THE INVENTION

Given the shortage of conventional energy sources (e.g., oil), many efforts have been spent on exploring alternative energy sources. Among them, plant biomass is of particular interest as it is renewable.

Plant mass contains a high amount of cellulose, a starting material for making biofuel. To convert cellulose to biofuel, it is first degraded to fermentable sugars, such as cellobiose and glucose, by the cellulolytic system of microorganisms. This system includes three major types of hydrolases, i.e., endo-glucanases (EC 3.2.1.4), exoglucanases (EC 3.2.1.91), and β-glucosidases (EC 3.2.1.21). Many cellulolytic enzymes have been isolated from various microorganisms, most of which exhibit optimal enzymatic activities at temperature below 50° C. As such, these enzymes do not efficiently degrade cellulose, the crystalline structure of which is typically destroyed above 50° C. Thus, there is a need for an efficient and thermophilic cellulolytic enzyme.

SUMMARY OF THE INVENTION

This invention is based on, at least in part, the discovery of a novel thermophilic endoglucanase isolated from *Geobacillus* sp. 70PC53, i.e., CelA. Shown in FIG. 1 are the polypeptide sequence of CelA and its cDNA sequence (SEQ ID NOs: 1 and 2, respectively)

Accordingly, one aspect of this invention features an isolated polypeptide containing a sequence exhibiting at least 70% (e.g., 80%, 90%, 95%, or 99%) amino acid identity to SEQ ID NO:1 as determined by the BLAST algorithm.

This invention also encompasses (i) an isolated nucleic acid including a nucleotide sequence that encodes the polypeptide described above, and (ii) a host cell containing such an isolated nucleic acid. In one example, the nucleotide sequence is SEQ ID NO: 2. The isolated nucleic acid of this invention can be an expression vector, in which the nucleotide sequence is operably linked to a suitable promoter sequence (i.e., a sequence capable of initiating transcription in a host cell).

The term "isolated polypeptide" or "isolated nucleic acid" used herein refers to a polypeptide or nucleic acid substantially free from naturally associated molecules, i.e., the naturally associated molecules constituting at most 20% by dry weight of a preparation containing the polypeptide or nucleic acid. Purity can be measured by any appropriate method, e.g., column chromatography, polyacrylamide gel electrophoresis, and HPLC.

Also within the scope of this invention is a method of producing a fermentable sugar from a lignocellulosic material. This method includes (i) providing a multi-enzyme composition containing the polypeptide described above, an exoglucanase, and a β-glucosidase, and (ii) contacting the multi-enzyme composition with a lignocellulosic material to produce a fermentable sugar, e.g., glucose, xylose, arabinose, galactose, mannose, rhamnose, sucrose, or fructose. The fermentable sugar can be converted to a fermentation product, such as alcohol, by microorganism fermentation or enzyme treatment. Examples of the lignocellulosic material used in this method include, but are not limited to, orchard prunings, chaparral, mill waste, urban wood waste, municipal waste, logging waste, forest thinnings, short-rotation woody crops, industrial waste, wheat, wheat straw, oat straw, rice straw, barley straw, rye straw, flax straw, soy hulls, rice hulls, oat hulls, sugar cane, corn, corn stover, corn stalks, corn gluten feed, corn cobs, corn husks, corn kernel, fiber from kernels, prairie grass, gamagrass, foxtail, sugar beet pulp, citrus fruit pulp, seed hulls, cellulosic animal wastes, lawn clippings, cotton, seaweed, trees, shrubs, grasses, sugar cane bagasse, products and by-products from wet or dry milling of grains, municipal solid waste, waste paper, yard waste, herbaceous material, agricultural residues, forestry residues, municipal solid wastes, waste paper, pulp, paper mill residues, branches, bushes, canes, corn, corn husks, energy crops, forests, fruits, flowers, grains, grasses, herbaceous crops, leaves, bark, needles, logs, roots, saplings, shrubs, switch grasses, trees, vegetables, fruit peels, vines, sugar beet pulp, wheat midlings, oat hulls, hard and soft woods, organic waste materials generated from agricultural processes, forestry wood waste, or combinations thereof.

The details of one or more embodiments of the invention are set forth in the description below. Other features or advantages of the present invention will be apparent from the following drawings and detailed description of an example, and also from the appended claims.

BRIEF DESCRIPTION OF THE DRAWINGS

The drawings are first described.

FIG. 1 is a diagram showing the polypeptide and coding sequences of CelA (SEQ ID NO:1 and SEQ ID NO:2, respectively).

DETAILED DESCRIPTION OF THE INVENTION

Described herein is an isolated polypeptide including an amino acid sequence at least 70% identical to that of CelA (SEQ ID NO:1) or a part thereof having at least 20 (e.g., 30, 50, 80, 100, 150, 200, 250, 300, and 350) contiguous amino acids. See Ng et al., *Extremophiles* 13:425-435 (2009). This polypeptide is an thermophilic endo-glucanase that hydrolyzes the 1,4-beta-D-glycosidic linkages in cellulose, lichenin, and cereal beta-D-glucans.

The "percent identity" of two amino acid sequences is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, wordlength=3 to obtain amino acid sequences homologous to the protein molecules of the invention. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

The isolated polypeptide can be prepared by purification from a suitable microorganism, e.g., *Geobacillus*. It also can be prepared via conventional recombinant technology. An example follows. A DNA fragment encoding CelA can be prepared by polymerase chain reaction from *Geobacillus* cells and cloned into an expression vector. Upon insertion, the CelA-encoding fragment is operably linked to a suitable promoter contained in the expression vector. The resultant DNA construct is then introduced into suitable host cells (e.g., *E. coli* cells, yeast cells, insect cells, and mammalian cells) for expression of CelA, which can be purified from the cells by conventional methods.

To make a functional equivalent of CelA, which is also within the scope of this invention, one or more conservative amino acid substitutions can be introduced into SEQ ID NO:1 without disrupting its endo-glucanase activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in SEQ ID NO:1 is preferably replaced with another amino acid residue from the same side chain family. Alternatively, mutations can be introduced randomly along all or part of SEQ ID NO:1, such as by saturation mutagenesis, and the resultant mutants can be screened for the endoglucanase activity to identify mutants that retain the activity as described below in the Example section below.

Fusion protein technology can be applied to improve expression efficiency and facilitate purification of the polypeptide of this invention. To prepare a fusion protein containing CelA, a DNA fragment encoding this endo-glucanase can be linked to another DNA fragment encoding a fusion partner, e.g., glutathione-s-transferase (GST), 6x-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention.

Also described herein is an isolated nucleic acid encoding the polypeptide of this invention. A nucleic acid refers to a DNA molecule (e.g., a cDNA or genomic DNA), an RNA molecule, or a DNA/RNA analog, which can be synthesized from nucleotide analogs. In one example, the nucleic acid of this invention is an expression vector in which a DNA fragment encoding the polypeptide is operably linked to a suitable promoter.

As used herein, the term "promoter" refers to a nucleotide sequence containing elements that initiate the transcription of an operably linked nucleic acid sequence in a desired host microorganism. At a minimum, a promoter contains an RNA polymerase binding site. It can further contain one or more enhancer elements which, by definition, enhance transcription, or one or more regulatory elements that control the on/off status of the promoter. When *E. coli* is used as the host microorganism, representative *E. coli* promoters include, but are not limited to, the β-lactamase and lactose promoter systems (see Chang et al., *Nature* 275:615-624, 1978), the SP6, T3, T5, and T7 RNA polymerase promoters (Studier et al., *Meth. Enzymol.* 185:60-89, 1990), the lambda promoter (Elvin et al., *Gene* 87:123-126, 1990), the trp promoter (Nichols and Yanofsky, *Meth. in Enzymology* 101:155-164, 1983), and the Tac and Trc promoters (Russell et al., *Gene* 20:231-243, 1982). When yeast is used as the host microorganism, exemplary yeast promoters include 3-phosphoglycerate kinase promoter, glyceraldehyde-3-phosphate dehydrogenase (GAPDH) promoter, galactokinase (GAL1) promoter, galactoepimerase promoter, and alcohol dehydrogenase (ADH) promoter. Promoters suitable for driving gene expression in other types of cells are also well known in the art.

A vector refers to a nucleic acid molecule capable of transporting another nucleic acid to which it has been linked. The vector can be capable of autonomous replication or integrate into a host DNA. Examples of the vector include a plasmid, cosmid, or viral vector. The vector of this invention includes a nucleotide sequence encoding CelA in a form suitable for expression of the nucleic acid in a host cell. Preferably the vector includes one or more regulatory sequences operatively linked to the encoding sequence. A "regulatory sequence" includes promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vector can be introduced into host cells to produce the polypeptide of this invention.

Also within the scope of this invention is a host cell that contains the above-described nucleic acid. Examples include *E. coli* cells, insect cells (e.g., using baculovirus expression vectors), yeast cells, plant cells, or mammalian cells. See e.g., Goeddel, (1990) *Gene Expression Technology*: Methods in Enzymology 185, Academic Press, San Diego, Calif. To produce a polypeptide of this invention, one can culture a host cell in a medium under conditions permitting expression of the polypeptide encoded by a nucleic acid of this invention, and purify the polypeptide from the cultured cell or the medium of the cell. Alternatively, the nucleic acid of this invention can be transcribed and translated in vitro, for example, using T7 promoter regulatory sequences and T7 polymerase.

Further described herein is a method of converting lignocellulosic material to fermentable products (e.g., fermentable sugars) using a multi-enzyme composition containing the endo-glycanase described herein and other cellulolytic enzymes, such as exo-glucanase and β-glucosidase. See, e.g., US Application Nos. 20070238155 and 20070250961. The term "cellulolytic enzyme" refers to an enzyme that hydrolyzes cellulose (a polysaccharide consisting of glucose units) into smaller sugar units. See Gilbert H J, Hazlewood G P, 1993 *J Gen Microbiol* 139:187-194; Olimiya K et al. 1997 *Biotechnol Genet Eng Rev.* 14:365-414. See also, e.g., US Application 2007016805. This multi-enzyme composition can be obtained from, e.g., a microbial, a plant, or a combination thereof, and will contain enzymes capable of degrading lignocellulosic material. In addition to the cellulolytic enzymes mentioned above, it can further include cellobiohydrolases, endoglucanase, beta-glucosidases), hemicellulases (such as xylanases, including endoxylanases, exoxylanase, and beta-xylosidase), ligninases, amylases, alpha-arabinofuranosidases, alpha-glucuronidases, alpha-glucuronidases, arabinases, glucuronidases, proteases, esterases (including ferulic acid esterase and acetylxylan esterase), lipases, glucomannanases, or xylogluconases.

As used herein the term "lignocellulosic material" refers to materials containing cellulose and/or hemicellulose. Generally, these materials also contain xylan, lignin, protein, and carbohydrates, such as starch and sugar. Lignocellulose is found, for example, in the stems, leaves, hulls, husks, and cobs of plants or leaves, branches, and wood of trees. The process of converting a complex carbohydrate (such as starch, cellulose, or hemicellulose) into fermentable sugars is also referred to herein as "saccharification." Fermentable sugars, as used herein, refer to simple sugars, such as glucose, xylose, arabinose, galactose, mannose, rhamnose, sucrose and fructose. Lignocellulosic material can include virgin plant biomass and/or non-virgin plant biomass such as agricultural biomass, commercial organics, construction and demolition debris, municipal solid waste, waste paper, and yard waste. Common forms of lignocellulosic material include trees, shrubs and grasses, wheat, wheat straw, sugar cane bagasse, corn, corn husks, corn kernel including fiber from kernels, products and by-products from milling of grains such as corn, rice, wheat, and barley (including wet milling and dry milling), as well as municipal solid waste, waste paper, and yard waste. The lignocellulosic material can also be, but is not limited to, herbaceous material, agricultural residues, forestry residues, and paper mill residues. "Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat midlings, oat hulls, hard and soft woods (not including woods with deleterious materials), organic waste materials generated from agricultural processes including farming and forestry activities, specifically including forestry wood waste, or a mixture thereof.

The fermentable sugar produced in the method described above can be converted to useful value-added fermentation products via enzyme treatment or chemical reaction. Examples of the fermentation product include, but are not limited to amino acids, vitamins, pharmaceuticals, animal feed supplements, specialty chemicals, chemical feedstocks, plastics, solvents, fuels, or other organic polymers, lactic acid, and ethanol, including fuel ethanol. Specific value-added fermentation products that may be produced by the methods of the invention include, but not limited to, biofuels (including ethanol and butanol); lactic acid; plastics; specialty chemicals; organic acids, including citric acid, succinic acid and maleic acid; solvents; animal feed supplements; pharmaceuticals; vitamins; amino acids, such as lysine, methionine, tryptophan, threonine, and aspartic acid; chemical feedstocks. The fermentable sugar can also be used for culturing microbes that produce fermentation products, e.g., industrial enzymes, such as proteases, cellulases, amylases, glucanases, lactases, lipases, lyases, oxidoreductases, transferases and xylanases.

The invention also provides a method of producing energy from lignocellulosic material. This method include providing the multi-enzyme composition described above; contacting the composition with the lignocellulosic material to produce a fermentable product; fermenting the fermentable product to produce a combustible fermentation product, and combusting the combustible fermentation product to produce energy. This method can be performed in a bioreactor that contains all necessary components and may preferably be configured for anaerobic growth of microorganisms. Methods for making and using bioreactors are known in the art. See, e.g., US Application 20080131958.

The polypeptide and composition described above can also be used in the paper and pulp industry. For example, they can be used in the deinking and refining of recycled paper. In this application, utilizing a thermostable cellulase, i.e. having optimal activity at temperatures of 65° C. or higher versus having optimal activity at room temperature, could reduce the amount of enzyme used per ton of paper substantially, and reduce the time of exposure to the enzyme needed to increase the brightness of the paper. Reducing the concentration of enzyme and the time of exposure to the enzyme in the refining process, correspondingly and desirably reduces the reaction of the cellulase on the fibrils themselves and processing costs.

The polypeptide of this invention has additional industrial applications where high temperatures are needed (e.g., clarification of fruit juices). Given its high thermostability (see the Example below), this polypeptide can function under high temperatures with no need to increase its amount. The polypeptide, in combination with other enzymes, can be used, with enhanced yields, in extracting juice from fruits, or extracting juice or soup flavorings from vegetables. In combination with protease, it can be used to dissociate dried seaweed, which is then fermented with alcohol to produce vinegar. The polypeptide, mixed with other enzymes, can also serve as a dough conditioner in the baking industry. See, e.g., U.S. Pat. No. 6,602,700

Moreover, the polypeptide of this invention can also be used in the textile industry. It can be used to brighten and soften cotton fabrics by removing microfibers on the surface, which causes a dull look of clothes. More specifically, it can be included as an additive in formulating enzyme-containing detergents for soil removal, fabric softening, and color brightening. For example, it can be used as a replacement to pumice in producing blue jeans having a "stone-washed" effect. Enzyme treatment causes less damage to the jean fabric than lengthy exposure to pumice. See U.S. Pat. Nos. 5,232,851, 5,677,151, 6,451,063, and 7,226,773.

In another aspect, the present invention provides a transgenic plant, the genome of which is augmented with a recombinant polynucleotide encoding a polypeptide of this invention operably linked to a promoter sequence. The polynucleotide is optimized for expression in the plant and the polypeptide is produced at a level greater than 5% total soluble protein, greater than 10% total soluble protein or greater than 20% total soluble protein. The polypeptide may be expressed constitutively or tissue-specifically. For example, it may be expressed in a plant tissue selected from the group consisting of stems and leaves. It may also be expressed in a targeted sub-cellular compartment or organelle, such as apoplast, chloroplast, cell wall, or vacuole. The plant may be a monocotyledonous plant or a dicotyledonous plant. In certain embodiments, the plant is a crop plant. The plant may be selected from the group consisting of corn, switchgrass, sorghum, miscanthus, sugarcane, poplar, pine, wheat, rice, soy, cotton, barley, turf grass, tobacco, bamboo, rape, sugar beet, sunflower, willow, and eucalyptus. Methods for making transgenic plants are well known in the art.

Without further elaboration, it is believed that one skilled in the art can, based on the above description, utilize the present invention to its fullest extent. The following specific example is, therefore, to be construed as merely illustrative, and not limitative of the remainder of the disclosure in any way whatsoever. All publications cited herein are incorporated by reference.

Cloning, Preparation, and Characterization of *Geobacillus* sp. 70PC53 Endo-Glucanase Isolation of *Geobacillus* Sp. 70PC53 from Rice Straw Compost A mixture of pig manure, pigbone powder, rice hull, and rice straw at a weight ratio of 3:1:12:6, was incubated at 55-70° C. to produce a rice straw compost. The rice straw compost (2 g) was mixed with rice hull (1 g) in 100 ml of minimal requirement (MR) medium (containing in one liter water, 1.4 g $(NH4)_2SO4$, 2.0 g $KH_2PO4$, 0.34 g $CaCl2.2H_2O$, 0.30 g $MgSO4.7H_2O$, 5 mg $FeSO4.7H_2O$, 1.6 mg $MnSO4.H_2O$, 1.4 mg $ZnSO_4.7H_2O$ and 2.0 mg $CoCl_2.6H_2$; see Mandels et al., J. Bacteriol 73:269-278, 1957) supplemented with 1.0 g carboxylmethyl cellulose (CMC). The mixture was incubated at 65° C. overnight (16 h) and its supernatant (100 ll) was placed on an MR-CMC plate (containing the MR medium supplemented with 1% CMC) and incubated at the same temperature for 24 h. Bacterial colonies grown on the MR-CMC plate were isolated, re-inoculated on a fresh MR-CMC plate, and incubated for a suitable period. The MR-CMC plate was then stained with a solution containing 0.2% Congo red solution and destained with a NaCl solution (1N). Bacterial colonies around which clear zones displayed, were chosen for further characterization. Identity of each isolated bacterial strain was analyzed by the 16S rDNA sequencing method described in Kim et al., Int. J. Syst. Evol. Microbiol. 50:1641-1647, 2000, using universal primers 27f: 5'-AGAGTTTGATCCTGGCTCAG-3' (SEQ ID NO:3) and 1497r: 5'-AAGTCGTAACAAGGTAACC-3' (SEQ ID NO:4).

The 16S rDNA analysis indicates that among all selected bacterial strains, over 100 are *Geobacillus* sp. strains. Strain 70PC53 was identified for exhibited high cellulolytic activity as evidenced by generation of a large-sized clear zone on the MR-CMC plate. Other features of this strain are described in Ng et al., Extremophiles 13:425-435, 2009.

Cloning of a Novel Endo-Glucanase CelA from *Geobacillus* Sp. 70PC53

Genomic DNA was purified from *Geobacillus* sp. 70PC53, partially digested with EcoRI, and resolved on a 0.8% agarose gel. DNA fragments ranging from 3 to 10 kb were recovered from the gel, cloned into pBluescriptII SK(+) (Stratagene, USA), and introduced into *E. coli* DH5a cells to generate a genomic library. Individual transformants were grown on Luria-Bertani (LB) agar plates containing 1.0% (w/v) CMC and 100 lg/ml ampicillin. Colonies that exhibited cellulolytic enzyme activity were identified following the method described above. Plasmid DNA of each positive clone was isolated and digested with EcoRI and HindIII to release the DNA fragment inserted therein. The DNA fragment was then inserted into the pBluescript vector, and subjected to DNA sequencing. One DNA fragment (1.104 bp) was found to encode a endo-glucanase (designated CelA endo-glucanase) having the amino acid sequence of SEQ ID NO:1.

Preparation of Recombinant CelA

The DNA fragment encoding CelA endo-glucanase was amplified by PCR, using forward primer, 5'-GGGAA CATATGGTGAAAAAAGCT TTTCTGCCCGTG-3' (SEQ ID NO:5; NdeI site underlined) and reverse primer, 5'-CGCCCCTCGAGCTCTTTGAACAAACGTT TCCCT-3' (SEQ ID NO:6; XhoI site underlined). The PCR product was inserted into the pET-20b(+) vector (encoding a His-tag) and introduced into *E. coli* strain Rosetta C41. A positive transformant was inoculated into 100 ml LB medium supplemented with 100 mg/ml ampicillin and cultured at 37° C. in a rotary shaker (150 rpm). When the $OD_{600}$ value of the cell culture reached 0.4 to 0.6, 1 mM of iso-propyl-b-thiogalactopyranoside (IPTG) was added to the culture to induce CelA expression. Six hours later, the bacterial cells were collected by centrifugation at 10,000 g, 4° C. for 15 min. After being washed with deionized water twice, the cells pellet were resuspended in a sodium phosphate buffer (pH 7.4) and disrupted by sonication. Upon centrifugation at 15,000 g, 4° C. for 20 min, the supernatant was collected and loaded onto a His-Trap affinity chromatography column (GE Health-care Bio-Sciences AB, Uppsala, Sweden). Fractions containing recombinant CelA (fused with a His-tag) were eluted with a sodium phosphate buffer (pH 7.4) containing 200 mM imidazole and 300 mM NaCl. Presence of CelA in these fractions was detected by SDS-PAGE analysis.

Characterization of CelA (1) Endo-Glucanase Activity

The endo-glucanase activity of CelA was determined by CMC zymogram analysis as described below. CelA was denatured by heating for 5 min at 100° C. in a solution containing 1% (w/v) SDS and 2% (w/v) DTT and then resolved on a 10% SDS-PAGE gel containing 0.2% (w/v) CMC. After electrophoresis, the gel was washed three times (each for 30 min) with 10 mM pH 8.0 Tris-HCl buffer containing 1% Triton X-100 and then soaked in the same buffer overnight to allow protein renaturation. Afterwards, the gel was incubated at 65° C. in 50 mM sodium acetate buffer (pH 5.0) for 30 min, stained with 0.2% (w/v) Congo red for 20 min, and destained with 1 M NaCl. A clear band against a red background was observed at the position corresponding to CelA, indicating that CelA possesses endo-glucanase activity.

Figure 2:
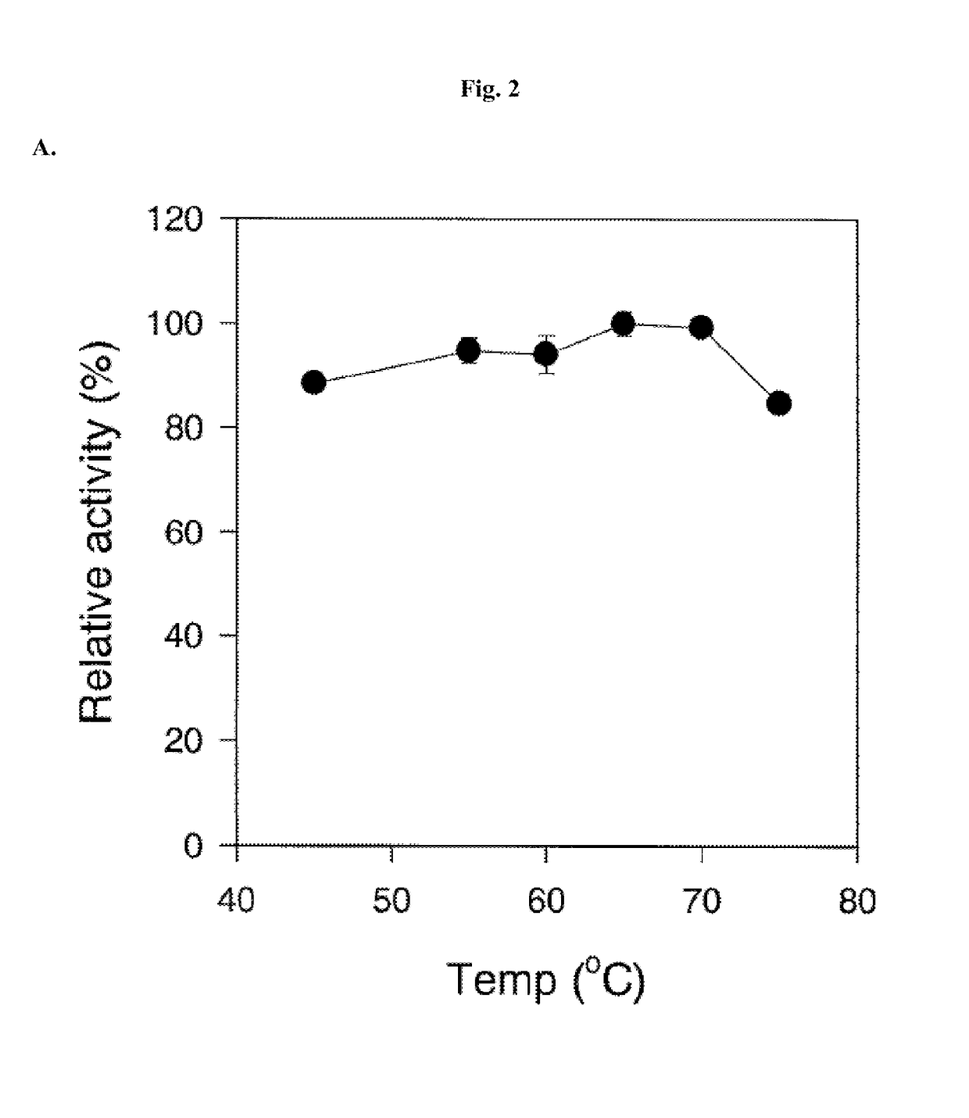
FIG. 2 is a diagram showing the optimal reaction temperature (panel A) and thermostability (panel B) of CelA.

The endo-glucanase activity of CelA was also determined following the method described in Miller et al., Anal Chem 31:426-428, 1959, under various conditions (i.e., temperature and pH value) to determine the optional reaction condition of this enzyme. Briefly, 0.5 ml of a solution containing CelA was mixed with 0.5 ml of 1.0% CMC in 50 mM sodium phosphate buffer at a test pH (i.e., pH 4-9). The mixture was incubation at a test temperature (i.e., 45, 55, 60, 65, 70, or 75° C.) for 15 min and the concentration of the reducing sugars (converted from CMC by CelA) was determined using the well-known dinitrosalicylic acid (DNS) method. One unit of enzyme activity refers to production of 1 µmol glucose per minute. The protein concentration of the CelA solution was determined by the Bradford method (see Bradford, Anal Biochem 72:248-254, 1976) using a Bio-Rad Protein Assay Kit. As shown in FIG. 2A, CelA was active in a broad temperature, i.e., 45-75° C.).

To determine its thermo-stability, CelA was incubated at 45, 55, 60, 65, 70 or 75° C. for 6 hours and its endo-glucanase activity was analyzed afterwards using 1.0% CMC in 50 mM sodium acetate buffer (pH 5.0). Over 80% of its endo-glucanase activity was maintained after 4-hour incubation at 75° C. (see FIG. 2B), indicating that CelA is a thermophilic enzyme.

Figure 3:
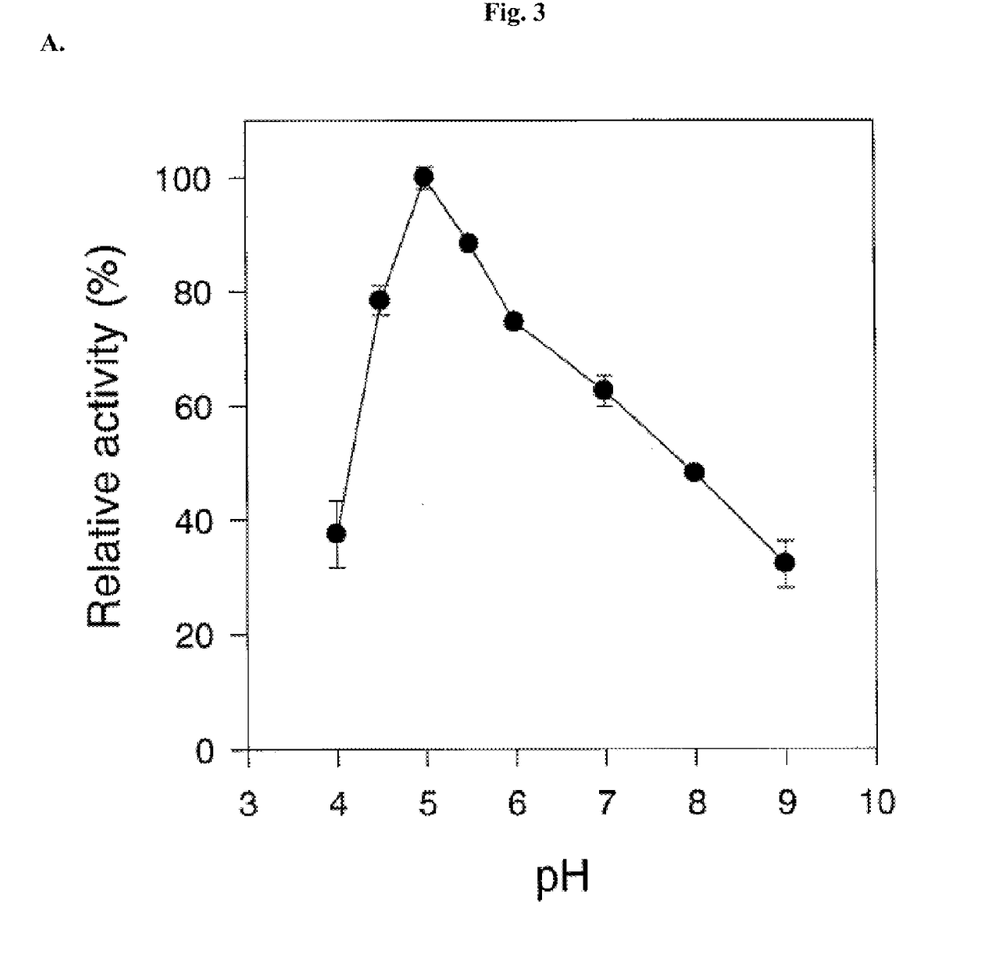
FIG. 3 is a diagram showing the optimal pH (panel A) and pH stability (panel B) of CelA.

The endo-glucanase activity of CelA was determined at various pH values, i.e., pH 4-5 (in sodium acetate buffer) and pH 6-9 (in sodium phosphate buffer). Further, CelA was incubated under various pH conditions (4-9) for 16 hours and its enzymatic activity was determined afterwards to examine its stability under different pH conditions. As shown in FIG. 3, CelA exhibits endo-glucanase activity in a broad pH range, i.e., pH 4-9 (see panel A) and remains stable after 16-hour incubation under the different pH conditions (see panel B).

Figure 4:
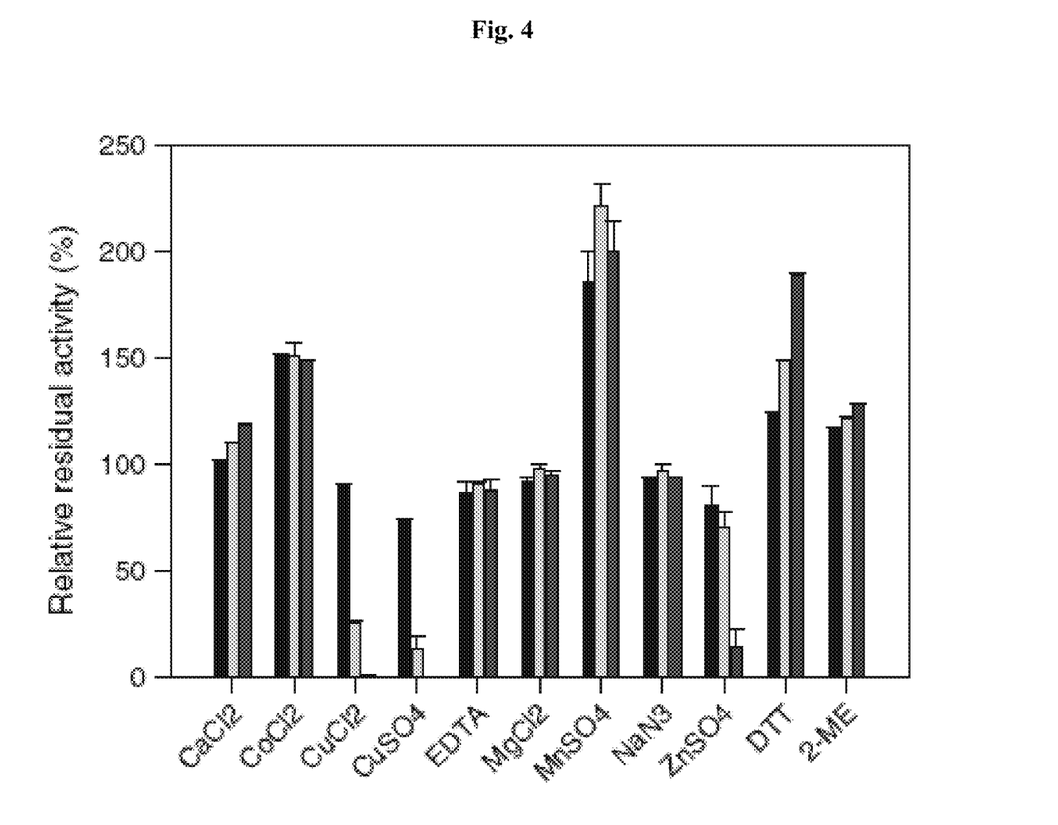
FIG. 4 is a chart showing effects of various chemicals on the endo-glucanase activity of CelA.

The endo-glucanase activity of CelA was determined in the presence of various chemicals, i.e., $CaCl_2$, $CoCl_2$, $CuCl_2$, $CuSO_4$, EDTA, $MgCl_2$, $MnSO_4$, $NaN_3$, $ZnSO_4$, DTT, and 2-mercaptoethanol, to examine the impact of these chemicals on CelA activity. Results indicate that certain divalent cations, i.e., $Mn^{2+}$, $Co^{2+}$, and $Ca^{2+}$, stimulate CelA activity. See FIG. 4.

(2) Substrate Specificity

The substrate specificity of CelA was analyzed at 65° C. using 1.0% of the various substrates listed below: Avicel, swollen Avicel, CMC, cellulose fiber, β-glucan (barely), filter paper, Lichenan, Xylan-brichwood and Xylan oat spelts. The results revealed that this enzyme efficiently hydrolyzes amorphous substrates, including Avicel, CMC, β-glucan and Lichenan. (Table 1).

TABLE 1

Substrate specificity of *Geobacillus* sp. 70PC53 Cel A in incubation at 65° C.

| Substrate | Specific activity (μmole glucose/mg/min) |
|---|---|
| Avicel | 0 |
| Acid swollen Avicel | 41.4 |
| CMC | 116.4 |
| Cellulose fiber | 0 |
| β-glucan (barely) | 1267.3 |
| Filter paper | 1.0 |
| Lichenan | 945.4 |
| Xylan-Brichwood | 5.3 |
| Xylan-oat spelts | 0.1 |

(3) Cellulolytic Activity Comparison Between CelA and *Trichoderma reesei* Celluloses Cellulases from *Trichoderma reesei* (ATCC 26921), substrates 4-nitrophenyl b-D-glucopyranoside (pNPG), 4-nitrophenyl b-D-cellobioside (pNPC) and 4-nitrophenyl b-D-cellotrioside (pNPT) were purchased from Sigma. The enzymatic activity of *T. reesei* cellulases and CelA were analyzed at a concentration of 1.0 mM using the different substrates listed above under at 37° C. and 65° C., respectively. 1 U of enzyme activity was defined as production of 1 μmol 4-nitrophenol under the reaction conditions described above.

As compared with *T. reesei* celluloses, CelA exhibited a tenfold greater enzymatic activity when CMC, pNPT and pNPC (all soluble) were used as substrates. See Table 2 below.

TABLE 2

Comparison of enzyme activity between CelA and *Trichoderma reesei* celluloses

| Substrate | Cel A (U/mg, 65° C.) | *T. reesei* Celluloses (U/mg, 37° C.) |
|---|---|---|
| CMC | 116.44 | 19.11 |
| Avicel | 0.71 | 3.84 |
| Filter paper | 1.06 | 19.13 |
| pNPT | 84.48 | 7.87 |
| pNPC | 166.89 | 13.61 |
| pNPG | 0.35 | 11.56 |
| β-1,3 Glucan (from *Euglena gracilis*) | 1.08 | 0.23 |

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An isolated nucleic acid, comprising a nucleotide sequence encoding an endo-glucanase having an amino acid sequence at least 95% identical to SEQ ID NO:1.

2. The isolated nucleic acid of claim 1, wherein the amino acid sequence is SEQ ID NO:1.

3. The nucleic acid of claim 1, wherein the nucleotide sequence is SEQ ID NO: 2.

4. A vector comprising the nucleic acid of claim 1 operably linked to a promoter.

5. The vector of claim 4, wherein the amino acid sequence is SEQ ID NO:1.

6. The vector of claim 4, wherein the nucleotide sequence is SEQ ID NO:2.

7. A host cell comprising the vector of claim 4.

8. The host cell of claim 7, wherein the amino acid sequence is SEQ ID NO:1.

9. The host cell of claim 7, wherein the vector comprises a nucleic acid that has the nucleotide sequence of SEQ ID NO:2 and is operably linked to a promoter.

10. A method of producing an endo-glucanase, the method comprising:
   culturing in a medium a host cell that contains an expression vector encoding an endo-glucanase under conditions permitting expression of the endo-glucanase, and
   isolating the endo-glucanase from the cultured cells, wherein the endo-glucanase is a polypeptide comprising an amino acid sequence at least 95% identical to SEQ ID NO: 1.

11. The method of claim 10, wherein the endo-glucanase has the amino acid sequence of SEQ ID NO:1.

* * * * *

SEQUENCE LISTING

<160> NUMBER OF SEQ ID NOS: 6

<210> SEQ ID NO 1
<211> LENGTH: 368
<212> TYPE: PRT
<213> ORGANISM: Geobacillus sp. 70PC53

<400> SEQUENCE: 1

Met Glu Arg Thr Pro Val Glu Glu Asn Gly Arg Leu Gln Val Val Gly
1               5                   10                  15

Thr Ala Leu Leu Asn Gln His Asn Lys Pro Phe Gln Leu Arg Gly Ile
            20                  25                  30

Ser Thr His Gly Leu Gln Trp Phe Gly Gln Phe Ala Asn Lys Asp Ala
        35                  40                  45

Phe Gln Thr Leu Arg Asp Asp Trp Lys Ala Asn Val Val Arg Leu Ala
    50                  55                  60

Met Tyr Thr Asp Pro Asn Ala Asn Gly Tyr Ile Ala Gln Pro Glu Trp
65                  70                  75                  80

Leu Lys Ala Lys Val Lys Glu Gly Val Gln Ala Ala Leu Asp Leu Gly
                85                  90                  95

Met Tyr Val Ile Ile Asp Trp His Ile Leu Asn Asp Asn Asp Pro Asn
            100                 105                 110

Leu Tyr Lys Glu Gln Ala Lys Arg Phe Phe Ala Glu Met Ala Arg Glu
        115                 120                 125

Tyr Gly Lys Tyr Pro Asn Val Ile Tyr Glu Ile Ala Asn Glu Pro Asn
    130                 135                 140

Gly Asn Asp Val Thr Trp Glu Glu Lys Ile Arg Pro Tyr Ala Asp Glu
145                 150                 155                 160

Val Ile Arg Thr Ile Arg Ser Ile Asp Arg Asp Asn Leu Ile Ile Val
                165                 170                 175

Gly Thr Gly Thr Trp Ser Gln Asp Val Asp Asp Val Ala Ser Asp Pro
            180                 185                 190

Leu Pro Tyr Lys Asn Ile Met Tyr Ala Val His Phe Tyr Ser Gly Thr
        195                 200                 205

His Thr Gln Trp Leu Arg Asp Arg Val Asp Ala Ala Leu Gln Ala Gly
    210                 215                 220

Thr Pro Val Phe Val Ser Glu Trp Gly Thr Ser Asp Ala Ser Gly Asp
225                 230                 235                 240

Gly Gly Pro Tyr Leu Glu Glu Ala Glu Lys Trp Ile Glu Phe Leu Asn
                245                 250                 255

Glu Arg Gly Ile Ser Trp Val Asn Trp Ser Leu Cys Asp Lys Asn Glu
            260                 265                 270

Ala Ser Ala Ala Leu Arg Pro Gly Ala Asp Pro His Gly Gly Trp Gly
        275                 280                 285

Asp Asp His Leu Ser Asp Ser Gly Arg Phe Ile Lys Ala Lys Leu Ile
    290                 295                 300

Glu Ala Ala Gln Gln Ser Gly Gln Lys Ala Lys Gly Ala Ala Asn Pro
305                 310                 315                 320

His Gln Arg Asn Gly Asn Asp Ser Ser Asp Gly Lys Thr Gly His
                325                 330                 335

Ala Ser Gly His Pro Phe Phe Trp Thr Phe Ile Leu Ala Ala Gly Val
        340                 345                 350

Ala Phe Gly Phe Gly Gly Leu Ala Leu Gly Lys Arg Leu Phe Lys Glu
        355                 360                 365

<210> SEQ ID NO 2
<211> LENGTH: 1104
<212> TYPE: DNA
<213> ORGANISM: Geobacillus sp. 70PC53

<400> SEQUENCE: 2

```
atggaacgca ccccggtgga agaaaacggc cgcctgcagg tggtgggcac cgcgctgctg    60
aaccagcata caaaccgtt tcagctgcgc ggcattagca cccatggcct gcagtggttt    120
ggccagtttg cgaacaaaga tgcgtttcag accctgcgcg atgattggaa agcgaacgtg    180
gtgcgcctgg cgatgtatac cgatccgaac gcgaacggct atattgcgca gccggaatgg    240
ctgaaagcga agtgaaaga aggcgtgcag gcggcgctgg atctgggcat gtatgtgatt    300
attgattggc atattctgaa cgataacgat ccgaacctgt ataagaaca ggcgaaacgc    360 ttttttgcgg aaatggcgcg cgaatatggc aaatatccga acgtgattta tgaaattgcg    420
aacgaaccga acggcaacga tgtgacctgg aagaaaaaa ttcgcccgta tgcggatgaa    480
gtgattcgca ccattcgcag cattgatcgc gataacctga ttattgtggg caccggcacc    540
tggagccagg atgtggatga tgtggcgagc gatccgctgc cgtataaaaa cattatgtat    600
gcggtgcatt tttatagcgg cacccatacc cagtggctgc gcgatcgcgt ggatgcggcg    660
ctgcaggcgg gcacccccggt gtttgtgagc gaatggggca ccagcgatgc gagcggcgat    720
ggcggcccgt atctggaaga agcggaaaaa tggattgaat tctgaacga acgcggcatt    780
```

-continued

```
agctgggtga actggagcct gtgcgataaa aacgaagcga gcgcggcgct gcgcccgggc      840
gcggatccgc atggcggctg gggcgatgat catctgagcg atagcggccg ctttattaaa      900
gcgaaactga ttgaagcggc gcagcagagc ggccagaaag cgaaaggcgc ggcgaacccg      960
catcagcgca acggcaacga tagcagcgat ggcggcaaaa ccggccatgc gagcggccat     1020
ccgttttttt ggacctttat tctggcggcg ggcgtggcgt ttggctttgg cggcctggcg     1080
ctgggcaaac gcctgtttaa agaa                                            1104

<210> SEQ ID NO 3
<211> LENGTH: 20
<212> TYPE: DNA
<213> ORGANISM: Artificial Sequence
<220> FEATURE:
<223> OTHER INFORMATION: PCR Primer

<400> SEQUENCE: 3
agagtttgat cctggctcag                                                   20

<210> SEQ ID NO 4
<211> LENGTH: 19
<212> TYPE: DNA
<213> ORGANISM: Artificial Sequence
<220> FEATURE:
<223> OTHER INFORMATION: PCR Primer

<400> SEQUENCE: 4
aagtcgtaac aaggtaacc                                                    19

<210> SEQ ID NO 5
<211> LENGTH: 35
<212> TYPE: DNA
<213> ORGANISM: Artificial Sequence
<220> FEATURE:
<223> OTHER INFORMATION: PCR Primer

<400> SEQUENCE: 5
gggaacatat ggtgaaaaaa gcttttctgc ccgtg                                  35

<210> SEQ ID NO 6
<211> LENGTH: 33
<212> TYPE: DNA
<213> ORGANISM: Artificial Sequence
<220> FEATURE:
<223> OTHER INFORMATION: PCR Primer

<400> SEQUENCE: 6
cgcccctcga gctctttgaa caaacgtttc cct                                    33
```